US012569230B2

(12) United States Patent
Boyle et al.

(10) Patent No.: US 12,569,230 B2
(45) Date of Patent: Mar. 10, 2026

(54) BIOPSY SYSTEM HAVING TISSUE SAMPLE IMPEDANCE MEASUREMENT

(71) Applicant: Bard Peripheral Vascular, Inc., Franklin Lakes, NJ (US)

(72) Inventors: Brian Boyle, Chandler, AZ (US); Bryon Pelzek, Gold Canyon, AZ (US); Ranjani Sampath Kumaran, Tempe, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 966 days.

(21) Appl. No.: 17/760,660

(22) PCT Filed: Sep. 20, 2019

(86) PCT No.: PCT/US2019/052180
§ 371 (c)(1),
(2) Date: Mar. 15, 2022

(87) PCT Pub. No.: WO2021/054974
PCT Pub. Date: Mar. 25, 2021

(65) Prior Publication Data
US 2022/0330929 A1      Oct. 20, 2022

(51) Int. Cl.
*A61B 10/02*      (2006.01)
*A61B 10/00*      (2006.01)

(52) U.S. Cl.
CPC ...... *A61B 10/0283* (2013.01); *A61B 10/0096* (2013.01); *A61B 2010/0208* (2013.01); *A61B 2562/0209* (2013.01); *A61B 2562/046* (2013.01)

(58) Field of Classification Search
CPC ............ A61B 10/0283; A61B 10/0096; A61B 2010/0208; A61B 2562/0209;
(Continued)

(56) References Cited

U.S. PATENT DOCUMENTS 5,810,742 A * 9/1998 Pearlman ........... A61B 17/3403
600/547
6,813,515 B2 11/2004 Hashimshony
(Continued)

FOREIGN PATENT DOCUMENTS

EP          0945103 A1 * 9/1999 ............. A61B 6/502
JP          2009225854 A       10/2009
(Continued)

OTHER PUBLICATIONS

Japanese Office Action dated Jun. 5, 2023 pertaining to Japanese application No. 2022-517828 filed Mar. 18, 2022, pp. 1-5.

*Primary Examiner* — Sean P Dougherty
(74) *Attorney, Agent, or Firm* — Dinsmore & Shohl LLP

(57) ABSTRACT

A biopsy system includes a biopsy probe configured to sever tissue to acquire a tissue sample. The biopsy probe has biopsy needle portion having a proximal end, a distal end, and a lumen. A vacuum source is coupled to the lumen. The vacuum source is configured to generate a vacuum to transport the tissue sample through the lumen and expel the tissue sample from the lumen at the proximal end of the biopsy needle portion. An arrangement of compression plates is configured to receive the tissue sample from the proximal end of the biopsy probe and is operable to compress the tissue sample. The arrangement of compression plates has a plurality of impedance measurement electrodes. An impedance measurement circuit is connected to the plurality of impedance measurement electrodes.

20 Claims, 6 Drawing Sheets

(58) Field of Classification Search
CPC ............ A61B 2562/046; A61B 5/0538; A61B
5/6848; A61B 10/0275; A61B 10/0266
See application file for complete search history.

(56) References Cited

U.S. PATENT DOCUMENTS

| | | | |
|---|---|---|---|
| 6,832,111 B2 | 12/2004 | Tu et al. | |
| 6,847,841 B1 | 1/2005 | El Hatw | |
| 7,505,811 B2 | 3/2009 | Hashimshony | |
| 7,758,601 B2 | 7/2010 | Heywang-Koebrunner et al. | |
| 7,904,145 B2 | 3/2011 | Hashimshony et al. | |
| 8,116,845 B2 | 2/2012 | Hashimshony et al. | |
| 8,195,282 B2 | 6/2012 | Hashimshony | |
| 8,449,477 B2 | 5/2013 | Hashimshony et al. | |
| 8,738,124 B2 | 5/2014 | Davies | |
| 9,226,979 B2 | 1/2016 | Hashimshony | |
| 9,492,130 B2 | 11/2016 | Flagle et al. | |
| 9,999,353 B2 | 6/2018 | Hashimshony et al. | |
| 2002/0052599 A1* | 5/2002 | Goble ................ | A61B 18/1445 606/51 |
| 2002/0107517 A1* | 8/2002 | Witt ................... | A61B 18/1442 606/50 |
| 2003/0078578 A1* | 4/2003 | Truckai ............. | A61B 18/1442 606/51 |
| 2005/0203441 A1 | 9/2005 | Voegele | |
| 2006/0079774 A1 | 4/2006 | Anderson | |
| 2007/0027514 A1* | 2/2007 | Gerber .................... | A61N 1/05 607/116 |
| 2010/0081964 A1 | 4/2010 | Mark et al. | |
| 2011/0105948 A1 | 5/2011 | Halter | |
| 2012/0123244 A1 | 5/2012 | Hashimshony et al. | |
| 2012/0123296 A1 | 5/2012 | Hashimshony et al. | |
| 2014/0163414 A1 | 6/2014 | Lee et al. | |
| 2014/0358447 A1* | 12/2014 | Doyle .................... | A61B 8/085 702/19 |
| 2015/0038872 A1 | 2/2015 | Halter | |
| 2015/0216442 A1 | 8/2015 | Lavy et al. | |
| 2015/0360224 A1* | 12/2015 | Zhang .................... | C12M 23/16 435/29 |
| 2016/0081585 A1 | 3/2016 | Halter | |
| 2016/0287135 A1 | 10/2016 | Park et al. | |
| 2017/0311935 A1 | 11/2017 | Choung et al. | |
| 2018/0049728 A1 | 2/2018 | Berlin et al. | |
| 2018/0136155 A1 | 5/2018 | Balthes et al. | |
| 2019/0038262 A1* | 2/2019 | Doyle .................... | A61B 6/502 |
| 2019/0201146 A1* | 7/2019 | Shelton, IV ..... | A61B 17/07207 |
| 2021/0196263 A1* | 7/2021 | Shelton, IV ..... | A61B 17/00234 |
| 2021/0318286 A1* | 10/2021 | Chen ................. | B01L 3/502715 |
| 2024/0108398 A1* | 4/2024 | Rioux ............... | A61B 18/1445 |
| 2024/0122494 A1* | 4/2024 | Bogdanowicz ...... | A61B 5/0538 |

FOREIGN PATENT DOCUMENTS

| | | | | |
|---|---|---|---|---|
| JP | 2010210588 A | | 9/2010 | |
| JP | 2018509605 A | | 4/2018 | |
| JP | 2021509603 A | * | 4/2021 | ..... A61B 17/320092 |
| WO | WO-2006113394 A2 | * | 10/2006 | ........... A61B 5/0261 |
| WO | WO-2011016034 A2 | * | 2/2011 | ........ A61B 10/0275 |
| WO | 2019117943 A1 | | 6/2019 | |

* cited by examiner

BIOPSY SYSTEM HAVING TISSUE SAMPLE IMPEDANCE MEASUREMENT

CROSS-REFERENCE TO RELATED APPLICATIONS

This application is a U.S. National Phase of International Application No. PCT/US2019/052180, entitled "Biopsy System having Tissue Sample Impedance Measurement" and filed Sep. 20, 2019, which is incorporated herein by reference in its entirety.

TECHNICAL FIELD

The present invention relates to a biopsy system, and, more particularly, to a biopsy system having tissue sample impedance measurement capability.

BACKGROUND ART

A biopsy procedure may be initiated after discovery of microcalcifications within a patient's breast based on mammography. The microcalcifications are small deposits of calcium oxalate or hydroxyapatite that are early indicators of potential cancerous tissue within the patient. A biopsy system includes a device for separating and collecting a tissue sample from a target site within a patient. One such biopsy system includes a driver component, and a probe component that is releasably secured to the driver component. The probe component has an elongated tubular section, a penetrating distal tip, and a tissue receiving aperture in the distal end of the tubular section proximal to the distal tip, and has a tissue cutting member which is slidably disposed within the probe member to cut a tissue specimen drawn into the interior of the device through the aperture by applying a vacuum to the inner lumen of the tissue cutting member. Current clinical practices typically include taking an x-ray of the collected tissue samples for confirmation of the microcalcifications following the biopsy procedure.

It is known to have a needle having impedance measurement capability, wherein the impedance of surrounding tissue may be measured. For example, as disclosed in International Pub. No. WO/2019/117943, corresponding to International Application No. PCT/US2017/066660, filed Dec. 15, 2017, a biopsy probe may include electrodes for measuring tissue impedance to facilitate tissue type determination and/or penetration depth measurements.

What is needed in the art is a biopsy system that can confirm the presence or absence of microcalcifications in an acquired tissue sample quickly and easily by the biopsy system during the biopsy procedure.

SUMMARY OF INVENTION

The present invention provides a biopsy system that can confirm of the presence or absence of microcalcifications in an acquired tissue sample quickly and easily by the biopsy system during the biopsy procedure.

The invention in one form is directed to a biopsy system that includes a biopsy probe configured to sever tissue to acquire a tissue sample. The biopsy probe has a biopsy needle portion that has a proximal end, a distal end, and a lumen. A vacuum source is coupled to the lumen. The vacuum source is configured to generate a vacuum to transport the tissue sample through the lumen and expel the tissue sample from the lumen at the proximal end of the biopsy needle portion. An arrangement of compression plates is configured to receive the tissue sample from the proximal end of the biopsy probe and is operable to compress the tissue sample. The arrangement of compression plates has a plurality of impedance measurement electrodes. An impedance measurement circuit is connected to the plurality of impedance measurement electrodes.

The invention in another form is directed to a biopsy system that includes a biopsy probe configured to sever tissue to acquire a tissue sample. The biopsy probe has a biopsy needle portion that has a proximal end, a distal end, and a lumen. A vacuum source is coupled to the lumen. The vacuum source is configured to generate a vacuum to transport the tissue sample through the lumen and expel the tissue sample from the lumen at the proximal end of the biopsy needle portion. A tissue sample collection receptacle is configured to receive the tissue sample at the proximal end of the biopsy probe. The tissue sample collection receptacle has an arrangement of compression plates. The arrangement of compression plates includes a movable compression plate and a stationary compression plate. The arrangement of compression plates is operable to compress the tissue sample between the movable compression plate and the stationary compression plate. A driver mechanism is configured to move the movable compression plate toward the stationary compression plate. A first subset of impedance measurement electrodes are on the movable compression plate. A second subset of impedance measurement electrodes are on the stationary compression plate. The second subset of impedance measurement electrodes is opposed to and faces the first subset of impedance measurement electrodes. An impedance measurement circuit is connected to the first subset of impedance measurement electrodes of the movable compression plate, and is connected to the second subset of impedance measurement electrodes of the stationary compression plate.

The invention in still another form is directed to a tissue impedance measuring device for a biopsy system. The tissue impedance measuring device includes a tissue sample collection receptacle configured to receive a tissue sample. The tissue sample collection receptacle has an arrangement of compression plates. The arrangement of compression plates includes a first compression plate and a second compression plate. The arrangement of compression plates is operable to compress the tissue sample between the first compression plate and the second compression plate. A driver mechanism is configured to move the first compression plate toward the second compression plate. A first subset of impedance measurement electrodes are on the first compression plate. A second subset of impedance measurement electrodes are on the second compression plate. The second subset of impedance measurement electrodes are opposed to and facing the first subset of impedance measurement electrodes. An impedance measurement circuit is connected to the first subset of impedance measurement electrodes of the first compression plate, and is connected to the second subset of impedance measurement electrodes of the second compression plate.

An advantage of the present invention is the ability to provide a confirmation of the presence or absence of microcalcifications in an acquired tissue sample during the biopsy procedure, which can potentially reduce the number of individual tissue samples needed, e.g., by ending the biopsy procedure as soon as microcalcifications are detected in the acquired tissue sample, which in turn reduces the overall time of the biopsy procedure, including less breast compression time and less needle time in the patient.

Another advantage is the ability to aid the user in distinguishing between different types of microcalcifications.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
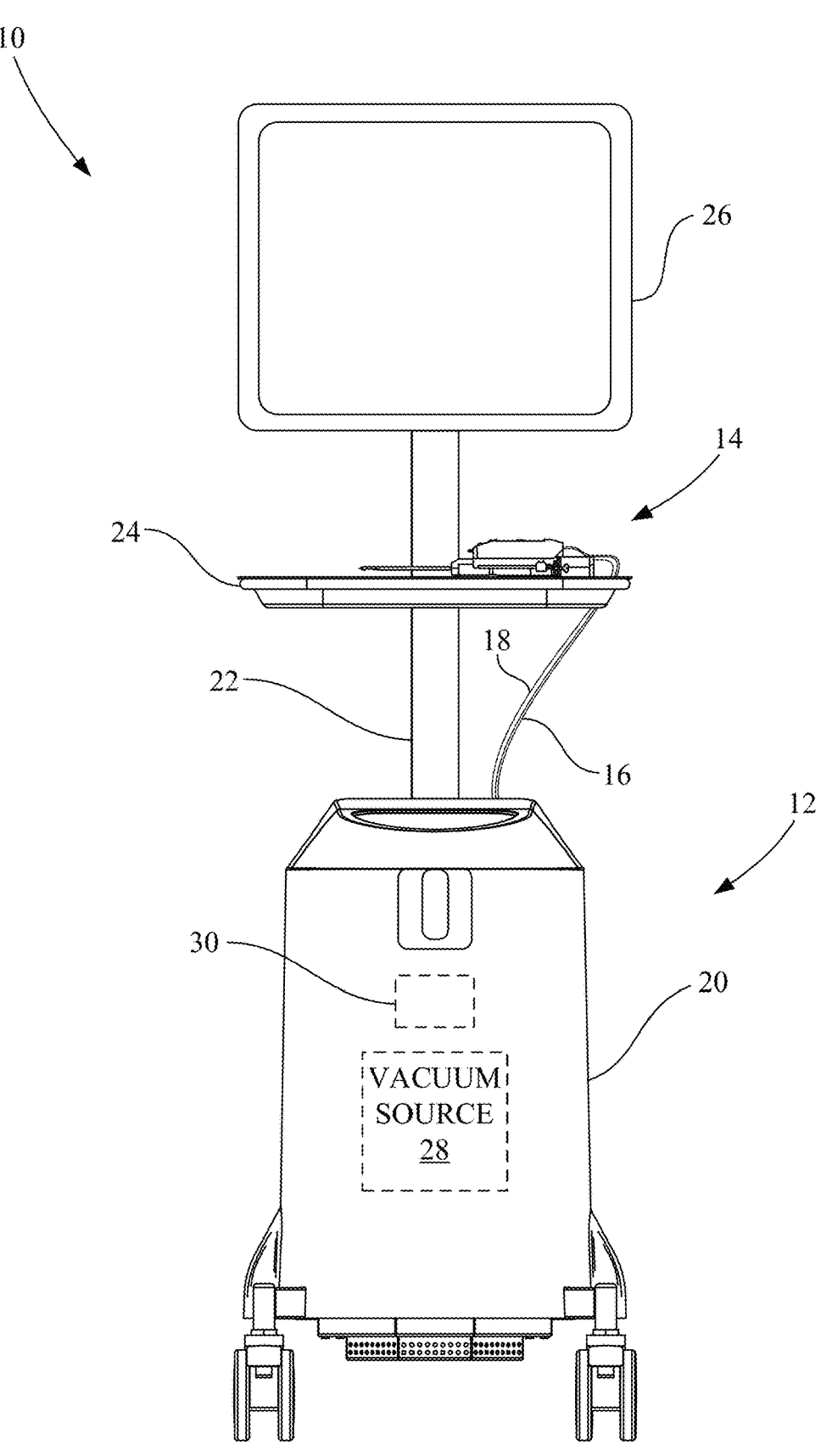
FIG. 1 is a front view of a biopsy system in accordance with an embodiment of the present invention.

Referring now to the drawings, and more particularly to FIG. 1, there is shown a biopsy system 10 in accordance with an embodiment of the present invention, which is configured to take impedance measurements of an acquired tissue sample during a biopsy procedure to confirm the presence or absence of one or more microcalcifications in the acquired tissue sample. In contrast to current clinical settings that use an x-ray of the samples for confirmation of micro-calcification following the biopsy procedure, advantageously, the present invention is able to provide a confirmation of the presence or absence of microcalcifications in the acquired tissue sample during the biopsy procedure, which can potentially reduce the number of individual tissue samples needed, e.g., by ending the biopsy procedure as soon as microcalcifications are detected in the acquired tissue sample, which in turn reduces the overall time of the biopsy procedure, including less breast compression time and less needle time in the patient.

Biopsy system 10 includes a console 12 and a biopsy instrument 14. Biopsy instrument 14 is connected to console 12 via an electrical cable 16 and a vacuum tube 18.

Console 12 includes a housing 20, a component mounting pole 22, an instrument tray 24, and a display screen 26.

Display screen 26 may be, for example, an LED monitor, LCD monitor, a laptop computer, or a tablet. Contained within housing 20 is a vacuum source 28 and a controller 30. Vacuum source 28 is in fluid communication with biopsy instrument 14 via vacuum tube 18. Controller 30 is electrically and communicatively coupled to controller 30 via electrical cable 16. Controller 30 also is electrically and communicatively coupled to display screen 26 via a separate electrical cable (not shown).

Vacuum source 28 includes a vacuum pump, such as a diaphragm or peristaltic pump.

Controller 30 may include, for example, a microprocessor and associated memory for executing program instructions to perform functions associated with biopsy procedure. For example, controller 30 is configured to execute program instructions to control operation of biopsy instrument 14 and vacuum source 28 for the retrieval and processing of one of acquired tissue samples. In addition, controller 30 also is configured to execute program instructions to generate messages, images, and icons on display screen 26.

Figure 2:
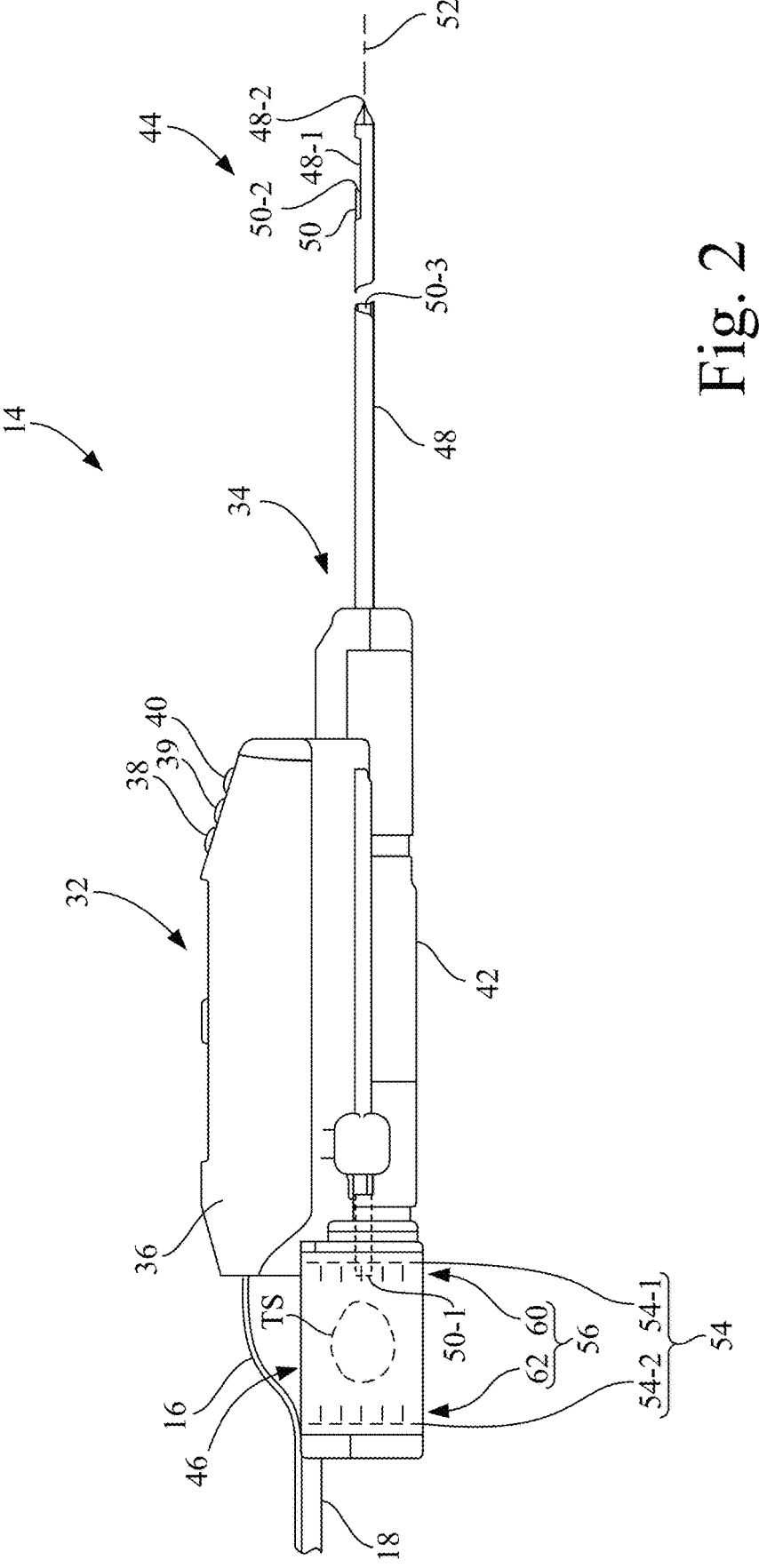
FIG. 2 is a side view of the biopsy instrument of the biopsy system of FIG. 1.

Referring also to FIG. 2, biopsy instrument 14 includes a handheld driver 32 and a biopsy probe 34. Biopsy probe 34 may be a disposable unit. The handheld driver 32 is releasably attached in driving engagement with biopsy probe 34. In particular, handheld driver 32 includes at least one electrical motor rotatably coupled to a drivetrain including one or more drive gears, and biopsy probe 34 includes a driven gear train including one or more driven gears that correspondingly engage the one or more drive gears of the drivetrain of handheld driver 32.

As depicted in FIG. 2, handheld driver 32 includes a driver housing 36, a sample switch 38, a vacuum switch 39, and a tissue impedance measurement switch 40. Each of sample switch 38, vacuum switch 39, and tissue impedance measurement switch 40 may be, for example, a push button.

Biopsy probe 34 includes a probe housing 42, a biopsy needle portion 44, and a tissue sample collection receptacle 46. Tissue sample collection receptacle 46 is coupled in fluid communication with vacuum source 28 via vacuum tube 18. Biopsy needle portion 44 includes a stylet 48, and a cutting cannula 50 arranged coaxial with stylet 48 along a longitudinal axis 52. In the present embodiment, tissue sample collection receptacle 46 receives a tissue sample from biopsy needle portion 44. However, it is contemplated that tissue sample collection receptacle 46 may be located in, or form a part of, biopsy needle portion 44. Also, while in the present embodiment tissue sample collection receptacle 46 is a part of biopsy instrument 14, it is contemplated that tissue sample collection receptacle 46 may be located in console 12.

Stylet 48 is in the form of a cannula that includes a sample notch 48-1, and a distal end 48-2. Distal end 48-2 is configured as a tapered piercing tip, which forms the distal end of biopsy needle portion 44. Stylet 48 is rotatable around longitudinal axis 52 via the driven gear train, so as to position sample notch 48-1 at each of a plurality of discrete angular positions about longitudinal axis 52.

Cutting cannula 50 includes a proximal end 50-1, a distal cutting end 50-2, and a lumen 50-3 that extends between proximal end 50-1 and distal cutting end 50-2. Proximal end 50-1 of cutting cannula 50 forms the proximal end of biopsy needle portion 44, and is received in tissue sample collection receptacle 46, such that lumen 50-3 of cutting cannula 50 is in fluid communication with vacuum source 28 via tissue sample collection receptacle 46. Cutting cannula 50 may have rotational motion, e.g., oscillating, and is axially slidable relative to sample notch 48-1 via the driven gear train between a retracted position, wherein sample notch 48-1 of stylet 48 is open to receive tissue at a biopsy site, and an extended position, which closes sample notch 48-1 of stylet 48.

A sample acquisition operation may be initiated by actuating sample switch 38, at which time cutting cannula 50 transitions from the retracted position to the extended position, which moves distal cutting end 50-2 of cutting cannula 50 to longitudinally pass across sample notch 48-1 to sever tissue received by sample notch 48-1 to acquire a tissue sample.

Upon actuation of vacuum source 28, e.g., automatically during the sample acquisition operation, or by manually actuating vacuum switch 39, the acquired tissue sample is transported via vacuum through lumen 50-3 of cutting cannula 50, and the acquired tissue sample is expelled from lumen 50-3 at proximal end 50-1 of cutting cannula 50 of biopsy needle portion 44 into tissue sample collection receptacle 46.

Figure 3:
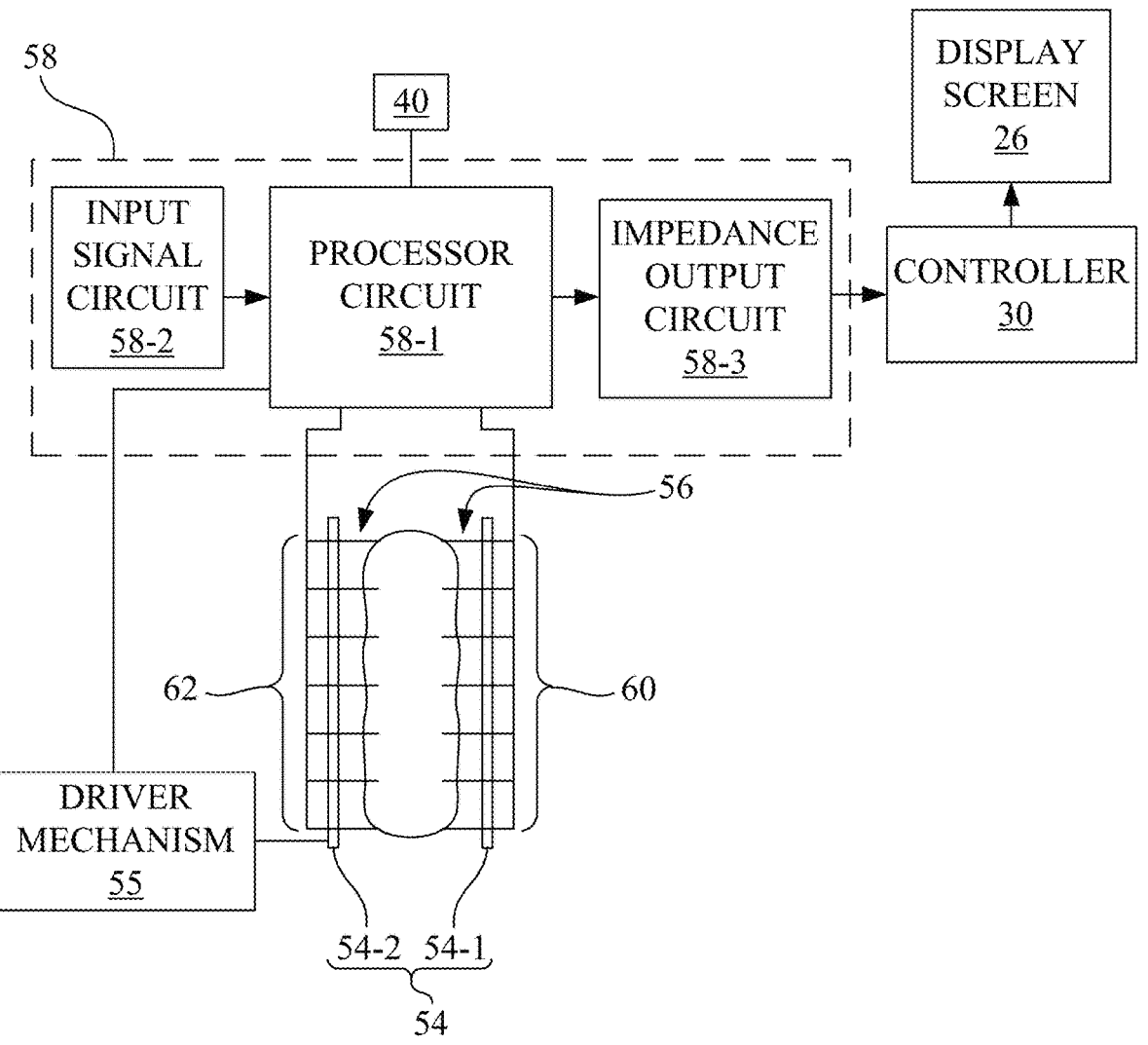
FIG. 3 is a block diagram depiction of the impedance measurement circuit, the arrangement of compression plates, and the plurality of impedance measurement electrodes, of the biopsy system of FIG. 1.

Referring to FIGS. 2 and 3, in accordance with an aspect of the present invention, biopsy instrument 14 includes an arrangement of compression plates 54 having a plurality of impedance measurement electrodes 56 that are electrically coupled to an impedance measurement circuit 58. Impedance measurement circuit 58 is electrically coupled to each of the plurality of impedance measurement electrodes 56. Impedance measurement circuit 58 is configured to actuate at least one pair of impedance measurement electrodes of the plurality of impedance measurement electrodes 56.

In the present embodiment, the arrangement of compression plates 54 is positioned in tissue sample collection receptacle 46, which is at a location distal to vacuum source 28. The arrangement of compression plates 54 is configured to receive the acquired tissue sample TS from proximal end 50-1 of cutting cannula 50 of biopsy probe 34, such that the tissue sample TS is expelled between two compression plates 54-1, 54-2 of the arrangement of compression plates 54. The arrangement of compression plates 54 is operable to compress the acquired tissue sample TS between the two compression plates 54-1, 54-2. As the arrangement of compression plates 54 compresses the tissue sample TS, the plurality of impedance measurement electrodes 56 contact, or contact and pierce, tissue sample TS.

Referring also to FIG. 3, the arrangement of compression plates 54 includes a first compression plate 54-1 and a second compression plate 54-2. Each of compression plates 54-1, 54-2 of the arrangement of compression plates 54 has at least one impedance measurement electrode of the plurality of impedance measurement electrodes 56. More particularly, the first compression plate 54-1 has a first subset of impedance measurement electrodes 60 of the plurality of impedance measurement electrodes 56, and the second compression plate 54-2 has a second subset of impedance measurement electrodes 62 of the plurality of impedance measurement electrodes 56. The first subset of impedance measurement electrodes 60 project in axial direction from the first compression plate 54-1, and the second subset of impedance measurement electrodes 62 project in an opposite axial direction from the second compression plate 54-2, such that the second subset of impedance measurement electrodes 62 are opposed to and facing the first subset of impedance measurement electrodes 60. Impedance measurement circuit 58 is electrically coupled to each of the first subset of impedance measurement electrodes 60 and the second subset of impedance measurement electrodes 62.

In the present embodiment, first compression plate 54-1 is a movable plate, and is sometimes referred to herein as movable compression plate 54-1. Second compression plate 54-2 is a stationary plate, and is sometimes referred to herein as stationary compression plate 54-2. A driver mechanism 55 is connected to the movable plate, e.g., movable compression plate 54-1. In the present embodiment, driver mechanism 55 is configured to move movable compression plate 54-1, e.g., axially along longitudinal axis 52, toward stationary compression plate 54-2 to compress the acquired tissue sample TS. Notwithstanding, it is contemplated that either or both of compression plates 54-1, 54-2 may be movable toward the other.

In one implementation, driver mechanism 55 includes a cylinder having a piston coupled to the movable compression plate 54-1 to move the movable compression plate 54-1, and the piston being moved via one of a pneumatic force, e.g., vacuum, and a hydraulic force. In another implementation, driver mechanism 55 may be an electromechanical device, such as a solenoid or motor drive. In still another implementation, driver mechanism 55 may be a mechanical device, e.g., having compression plate slider guides and/or a gear train, which may facilitate manual movement of either or both of compression plates 54-1, 54-2.

Referring particularly to FIG. 3, impedance measurement circuit 58 is electrically and individually connected to each impedance electrode of the plurality of impedance measurement electrodes 56. In the present embodiment, impedance measurement circuit 58 is located on biopsy instrument 14, e.g., on handheld driver 32 and/or biopsy probe 34. However, it is contemplated that, alternatively, impedance measurement circuit 58 may be located in console 12, if desired.

Impedance measurement circuit 58 includes a processor circuit 58-1, an input signal circuit 58-2, and an impedance output circuit 58-3.

Processor circuit 58-1 includes a microprocessor, associated memory, and associated input/output circuits. Processor circuit 58-1 is electrically and communicatively coupled to each of tissue impedance measurement switch 40 and driver mechanism 55. Processor circuit 58-1 is configured to execute program instructions to take impedance measurements from various regions of an acquired tissue sample TS. Upon activation of tissue impedance measurement switch 40, processor circuit 58-1 executes program instructions to activate driver mechanism 55 to compress the acquired tissue sample TS between compression plates 54-1, 54-2, and to begin taking impedance measurements of the compressed tissue sample TS.

More particularly, in the present embodiment, processor circuit 58-1 executes program instructions to activate at least one impedance measurement electrode from the first subset of impedance measurement electrodes 60 of first compression plate 54-1, and to activate at least one impedance measurement electrode from the second subset of impedance measurement electrodes 62 of second compression plate 54-2, to facilitate impedance measurement.

Input signal circuit 58-2 generates a radio frequency signal at a particular fixed frequency, or alternatively, a range of varying frequencies, which is supplied to the first subset of impedance measurement electrodes 60, passes through the acquired tissue sample TS, and then returns via the second subset of impedance measurement electrodes 62. For example, the current of varying frequencies may be supplied onto the tissue (e.g., at frequencies between 100 Hz to 1 KHz), and the varying voltages may be measured to calculate the impedances. In one implementation, for example, processor circuit 58-1 routes the radio frequency signal through each predefined pair of impedance measurement electrodes of the subsets of impedance measurement electrodes 60, 62, so as to take individual impedance measurements of selected regions of the acquired tissue sample TS. In the present embodiment, impedance output circuit 58-3 is configured as a voltage/current detector circuit that converts the received voltage/current signal to an impedance value, which may then be supplied to controller 30, which in turn executes program instructions to display the impedance measurements at display screen 26. However, it is contemplated that, alternatively, other types of output circuits might be used, such as for example, a Wheatstone bridge, a voltage comparator, or other resonance or r.f. methods.

Figure 4:
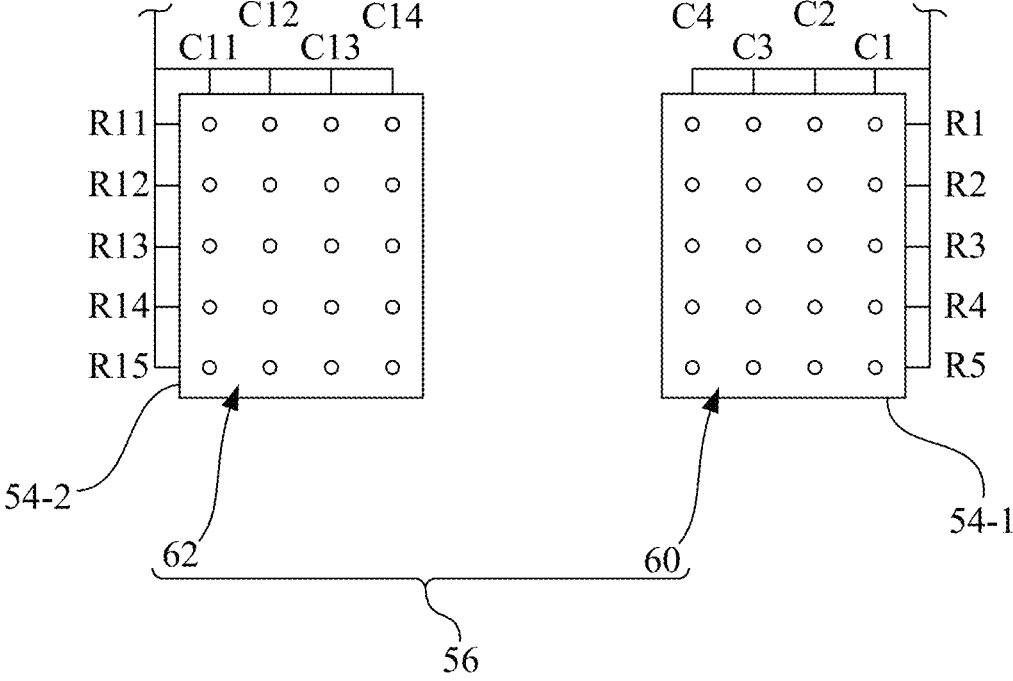
FIG. 4 is a diagrammatic representation of the respective array pattern of a subset of impedance measurement electrodes on each of the compression plates of the arrangement of compression plates of FIG. 3.

Referring also to FIG. 4, the first subset of impedance measurement electrodes 60 is arranged in a first array pattern and the second subset of impedance measurement electrodes 62 is arranged in a second array pattern. In the present embodiment, each of the first array pattern of the first subset of impedance measurement electrodes 60 and the second array pattern of the second subset of impedance measurement electrodes 62 include an equal number of opposed impedance measurement electrodes.

In the present embodiment, each of the first array pattern and the second array pattern are arranged in a rectangular matrix indexable by row and column coordinates. More particularly, in this example, the first array pattern of the first subset of impedance measurement electrodes 60 includes rows R1, R2, R3, R4, R5 and columns C1, C2,C3, C4. The second array pattern of the second subset of impedance measurement electrodes 62 includes rows R11, R12, R13, R14, R15 and columns C11, C12, C13, C14.

In the arrangement of compression plates 54-1, 54-2 depicted in FIGS. 2-4, the first subset of impedance measurement electrodes 60 of the first array pattern is opposed to the second subset of impedance measurement electrodes 62 of the second array pattern. For example, referring again to FIG. 4, if an impedance reading is desired in the central-right-upper region of compression plate 54-1, then processor circuit 58-1 may activate electrode R2, C2 of compression plate 54-1 and the opposed electrode R12, C12 of compression plate 54-2.

Processor circuit 58-1 may further execute program instructions to sequentially activate opposed pairs of impedance measurement electrodes of the first subset of impedance measurement electrodes 60 and the second subset of impedance measurement electrodes 62, e.g., electrode pairs [R1,C1;R11,C11]; [R1,C2;R11,C12]; [R1,C3;R11,C13] . . . [R5,C4;R15,C14]. By sequentially indexing through the row-column opposed pairs combinations, an impedance reading of all regions of the acquired tissue sample TS may be achieved, and presented as an impedance measurement collection on display screen 26 in the form of a 2D impedance map for analysis and comparison by the operator.

Figure 5A:
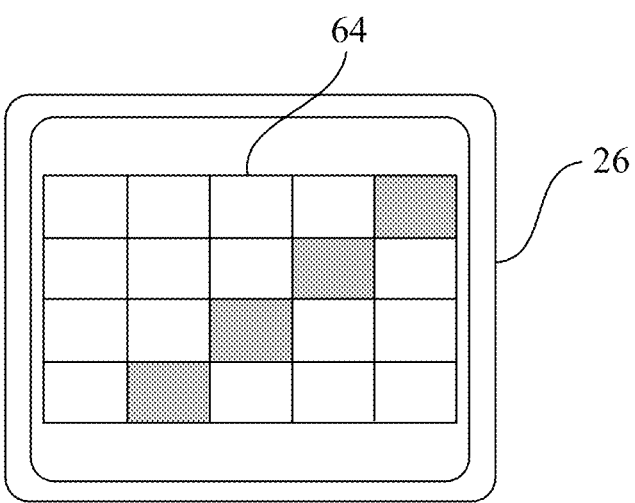
FIG. 5A is a diagrammatic representation of a display screen of the biopsy system of FIG. 1, displaying an impedance map in the form of a rectangular grid matrix having a plurality of rectangular elements.
Figure 5B:
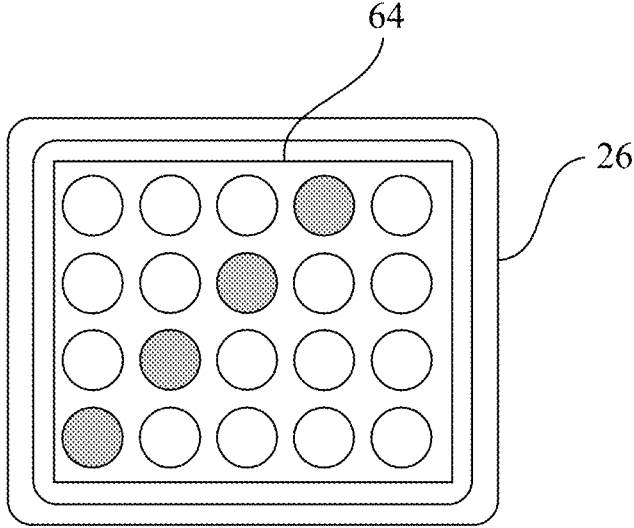
FIG. 5B is a diagrammatic representation of a display screen of the biopsy system of FIG. 1, displaying an impedance map in the form of a rectangular grid matrix having a plurality of circular elements.

For example, referring also to FIGS. 5A and 5B, there is shown an impedance map 64, generated on display screen 26, which includes an impedance measurement collection of the measured data generated from the plurality of impedance measurement electrodes 56. In the present embodiment, impedance map 64 may be in the form of a 2D grid matrix. However, it is contemplated that other graphical representations may be used to represent the impedance measurement data, such as for example, a line graph, a bar graph, or pictorial, etc. Impedance map 64 represents tissue impedance measurements of multiple regions of the acquired tissue sample TS, wherein each darkened area, e.g., rectangle or circle (dot), represents a microcalcification presence. Thus, impedance map 64 depicts the presence and absence of microcalcifications across tissue sample TS, relating to a plurality of locations in the tissue sample TS as measured by the 2D matrix of electrodes 56, so as to aid the user in distinguishing between healthy tissue and microcalcifications, and to provide positional information regarding the locations of the microcalcifications in the tissue sample TS.

Also, such a display of impedance map 64 that includes the impedance measurement collection may further be used to aid the user in distinguishing between different types of microcalcifications. For example, there are two types of microcalcifications, namely, Calcium Oxalate (type I) and Calcium Phosphate composites, which are calcium hydroxyapatite usually (type II). These can be differentiated through bio-impedance identification providing distinct ranges of impedance for each type, so as to differentiate type I vs type II microcalcifications, which in turn helps in the screening of benign vs cancerous microcalcifications, respectively. In turn, the two different types of calcifications may be displayed on display screen 26 as two different colors, shades, or patterns within the darkened areas, e.g., rectangles or circles (dots), in the 2D grid matrix of impedance map 64.

Alternatively, it is contemplated that processor circuit 58-1 may execute program instructions to simultaneously activate multiple opposed, or not opposed, pairs of impedance measurement electrodes of the first subset of impedance measurement electrodes 60 and the second subset of impedance measurement electrodes 62, if desired, to take impedance measurements across a broader region of tissue sample TS.

As a further alternative, it is contemplated that processor circuit 58-1 may execute program instructions to activate a pair of impedance measurement electrodes from just one of the compression plates, e.g., one of first compression plate 54-1 and second compression plate 54-2, to facilitate impedance measurement of the portion of the tissue sample between the activated pair of impedance measurement electrodes on the one compression plate. For example, processor circuit 58-1 may execute program instructions to activate a pair of impedance measurement electrodes from the first subset of impedance measurement electrodes 60 of first compression plate 54-1 for impedance measurement. In this example, multiple impedance measurements may be taken across the tissue sample TS by sequentially selecting different pairs of impedance measurement electrodes from the first subset of impedance measurement electrodes 60.

While in the present embodiment the tissue sample collection receptacle 46, the arrangement of compression plates 54, the plurality of impedance measurement electrodes 56, and the impedance measurement circuit 58 are located in biopsy instrument 14, it is contemplated that these components may alternatively be located in console 12. Further, it is contemplated that these components may be located in, on, or form a part of, biopsy probe 34, and may be located in, or form a part of, biopsy needle portion 44.

Figure 6:
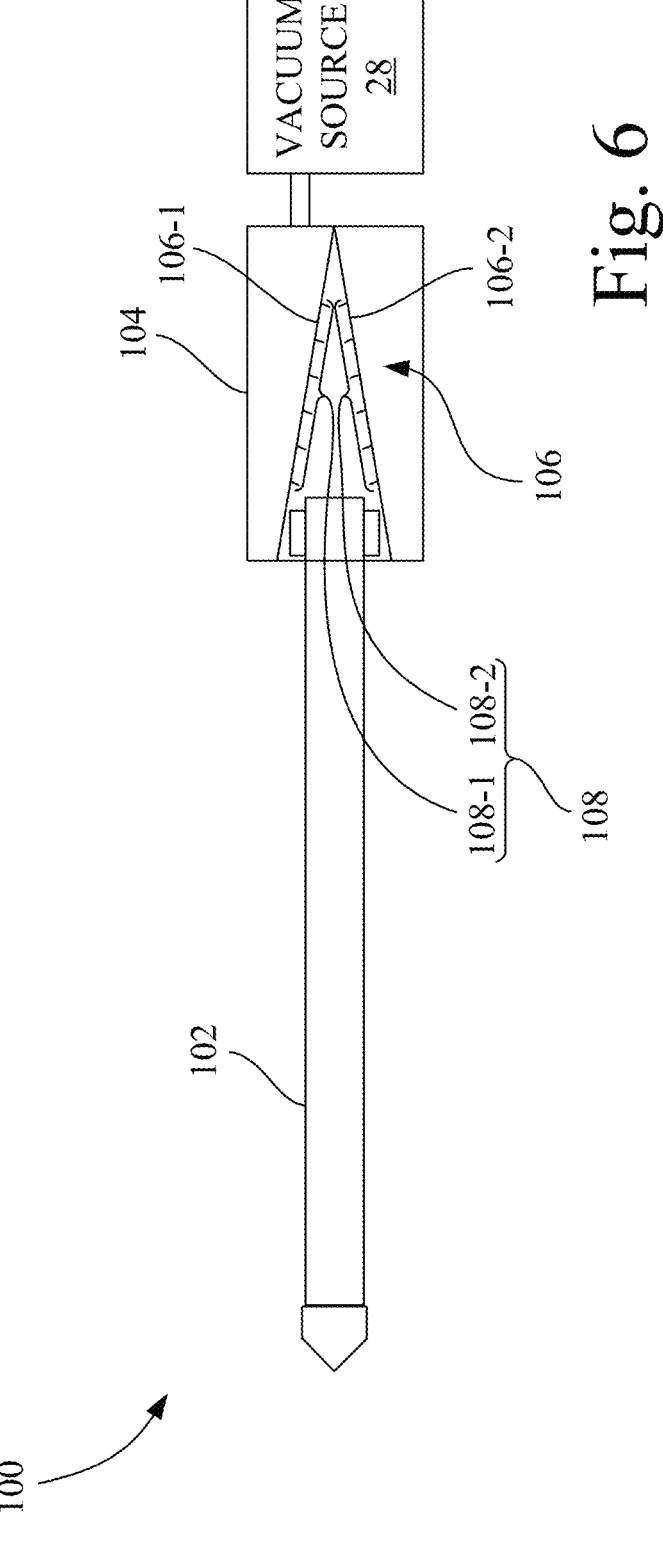
FIG. 6 is a diagrammatic representation of another embodiment of a biopsy instrument configured to take impedance measurements of an acquired tissue sample during a biopsy procedure, wherein a plurality of impedance measurement electrodes are arranged on a funneling frame.

FIG. 6 is a diagrammatic representation of another embodiment of a biopsy instrument 100 configured to take impedance measurements of an acquired tissue sample during a biopsy procedure.

Biopsy instrument 100 includes a biopsy probe 102, a tissue sample collection receptacle 104, and vacuum source 28 (described above). Tissue sample collection receptacle 104 contains a funneling frame 106. In the present embodiment, funneling frame 106 is in the form of a V-shaped structure having a first plate 106-1 and a second plate 106-2. First plate 106-1 and second plate 106-2 may be stationary, or alternatively, movable. Each of first plate 106-1 and second plate 106-2 may be a solid plate, or alternatively, may be in the form of a plate having a plurality of openings or pores. Also, each of first plate 106-1 and second plate 106-2 may be flat, or may be curved lengthwise and/or widthwise.

A plurality of impedance measurement electrodes 108 is arranged on funneling frame 106. The plurality of impedance measurement electrodes 108 includes a first subset of impedance measurement electrodes 108-1 and a second subset of impedance measurement electrodes 108-2. The first subset of impedance measurement electrodes 108-1 is located on first plate 106-1 and the second subset of impedance measurement electrodes 108-2 is located on second plate 106-2.

Referring also to FIG. 3, the first subset of impedance measurement electrodes 108-1 and the second subset of impedance measurement electrodes 108-2 may be connected to impedance measurement circuit 58 in a manner similar to that of the subsets of impedance measurement electrodes 60, 62. For brevity, the description and operation of impedance measurement circuit 58 will not be repeated here.

In operation, vacuum generated by vacuum source 28 pulls the sample from biopsy probe 102 into tissue sample collection receptacle 104, wherein the tissue sample is received in the V-shape of funneling frame 106. The first subset of impedance measurement electrodes 108-1 and the second subset of impedance measurement electrodes 108-2, connected to impedance measurement circuit 58, then measure the tissue impedance(s) of the biopsied tissue sample at multiple locations.

As an alternative to the V-shape of funneling frame 106 having open sides, it is contemplated that funneling frame 106 may have other funneling shapes, such as a frustoconical arrangement of curved plates as first plate 106-1 and second plate 106-2 of funneling frame 106.

The following items also relate to the invention:

In one form, the invention relates to a biopsy system. The biopsy system includes a biopsy probe, a vacuum source, an arrangement of compression plates, and an impedance measurement circuit. The biopsy probe is configured to sever tissue to acquire a tissue sample. The biopsy probe has a biopsy needle portion. The biopsy needle portion may have a proximal end, a distal end, and a lumen. The vacuum source is (or is configured to be) coupled to the lumen. The vacuum source is configured to generate a vacuum to transport the tissue sample through the lumen and expel the tissue sample from the lumen at the proximal end of the biopsy needle portion. The arrangement of compression plates is configured to receive the tissue sample from the proximal end of the biopsy probe. The arrangement of compression plates is configured to compress the tissue sample. The arrangement of compression plates has a plurality of impedance measurement electrodes. The impedance measurement circuit is connected to the plurality of impedance measurement electrodes.

In some embodiments, for example, the arrangement of compression plates may be located in a tissue sample collection receptacle, which may be comprised in the biopsy probe.

In some embodiments, for example, the arrangement of compression plates may be located distal to the vacuum source.

In some embodiments, for example, the arrangement of compression plates may include at least one movable plate and a driver mechanism. The driver mechanism may be configured to move each movable plate to effect compression of the tissue sample.

In some embodiments, for example, the arrangement of compression plates may include a movable plate, a stationary plate, and a driver mechanism, wherein the driver mechanism is configured to move the movable plate toward the stationary plate.

In some embodiments, for example, the driver mechanism may include a cylinder having a piston coupled to the movable plate to move the movable plate, wherein the piston may be moved via one of a pneumatic force and a hydraulic force.

In some embodiments that include the driver mechanism, the driver mechanism may be one of a mechanical device and an electromechanical device.

In any of the preceding embodiments, each compression plate of the arrangement of compression plates has at least one impedance measurement electrode.

In some embodiments, for example, one compression plate of the arrangement of compression plates may have at least two impedance measurement electrodes.

In any of the preceding embodiments, the impedance measurement circuit is electrically coupled to each of the plurality of impedance measurement electrodes, wherein the impedance measurement circuit is configured to actuate at least one pair of impedance measurement electrodes of the plurality of impedance measurement electrodes.

In some embodiments, for example, the arrangement of compression plates may include a first compression plate and a second compression plate, optionally wherein the first compression plate has a first subset of impedance measurement electrodes of the plurality of impedance measurement electrodes, and the second compression plate has a second subset of impedance measurement electrodes of the plurality of impedance measurement electrodes.

In the embodiment of the immediately preceding paragraph, the impedance measurement circuit is electrically coupled to each of the first subset of impedance measurement electrodes and the second subset of impedance measurement electrodes. Optionally, the impedance measurement circuit may have a processor circuit that is configured to execute program instructions to activate at least one impedance measurement electrode from the first subset of impedance measurement electrodes and to activate at least one impedance measurement electrode from the second subset of impedance measurement electrodes, to facilitate impedance measurement.

In any of the embodiments having the first subset of impedance measurement electrodes and the second subset of impedance measurement electrodes, the first subset of impedance measurement electrodes may be arranged in a first array pattern and the second subset of impedance measurement electrodes may be arranged in a second array pattern.

In any of the embodiments having the first subset of impedance measurement electrodes and the second subset of impedance measurement electrodes, the first subset of impedance measurement electrodes of the first array pattern is opposed to the second subset of impedance measurement electrodes of the second array pattern. The processor circuit may be configured execute program instructions to sequentially activate opposed pairs of impedance measurement electrodes of the first subset of impedance measurement electrodes and the second subset of impedance measurement electrodes.

In some embodiments having the first subset of impedance measurement electrodes and the second subset of impedance measurement electrodes, the processor circuit may be configured execute program instructions to simultaneously activate multiple opposed pairs of impedance measurement electrodes of the first subset of impedance measurement electrodes and the second subset of impedance measurement electrodes.

In another form, the invention also relates to a biopsy system. The biopsy system may include a biopsy probe, a vacuum source, a tissue sample collection receptacle, a driver mechanism, a first subset of impedance measurement electrodes, a second subset of impedance measurement electrodes, and an impedance measurement circuit. The biopsy probe is configured to sever tissue to acquire a tissue sample. The biopsy probe has a biopsy needle portion. The biopsy needle portion may have a proximal end, a distal end, and a lumen. The vacuum source is (or is configured to be) coupled to the lumen. The vacuum source is configured to generate a vacuum to transport the tissue sample through the lumen and expel the tissue sample at the lumen at the proximal end of the biopsy needle portion. The tissue sample collection receptacle is configured to receive the tissue sample from the proximal end of the biopsy probe. The tissue sample collection receptacle has an arrangement of compression plates. The arrangement of compression plates may include a movable compression plate and a stationary compression plate. The arrangement of compression plates are configured to compress the tissue sample between the movable compression plate and the stationary compression plate. The driver mechanism is configured to move the movable compression plate toward the stationary compression plate. The first subset of impedance measurement electrodes are on the movable compression plate. The second subset of impedance measurement electrodes are on the stationary compression plate. The second subset of impedance measurement electrodes are opposed to and face the first subset of impedance measurement electrodes. The impedance measurement circuit is connected to the first subset of impedance measurement electrodes of the movable compression plate, and is connected to the second subset of impedance measurement electrodes of the stationary compression plate. This biopsy system may include the tissue impedance measuring device of embodiments described below and a biopsy probe configured to sever tissue to acquire a tissue sample, the biopsy probe having a biopsy needle portion, the biopsy needle portion having a proximal end, a distal end, and a lumen, as well as a vacuum source (configured to be) coupled to the lumen, the vacuum source configured to generate a vacuum to transport the tissue sample through the lumen and expel the tissue sample at the lumen at the proximal end of the biopsy needle portion.

In some embodiments, as in the embodiment of the immediately preceding paragraph, for example, the impedance measurement circuit is electrically coupled to each of the first subset of impedance measurement electrodes and the second subset of impedance measurement electrodes. The impedance measurement circuit may have a processor circuit that may be configured to execute program instructions to activate at least one impedance measurement electrode from the first subset of impedance measurement electrodes and to activate at least one impedance measurement electrode from the second subset of impedance measurement electrodes, to facilitate impedance measurement.

In some embodiments, as in the embodiments of the immediately preceding two paragraphs, for example, the first subset of impedance measurement electrodes may be arranged in a first array pattern and the second subset of impedance measurement electrodes may be arranged in a second array pattern.

In some embodiments, as in the embodiment of the immediately preceding paragraph, for example, the first subset of impedance measurement electrodes of the first array pattern is opposed to the second subset of impedance measurement electrodes of the second array pattern. The processor circuit may be configured to execute program instructions to sequentially activate opposed pairs of impedance measurement electrodes of the first subset of impedance measurement electrodes and the second subset of impedance measurement electrodes.

In some embodiments, the processor circuit may be configured to execute program instructions to simultaneously activate multiple opposed pairs of impedance measurement electrodes of the first subset of impedance measurement electrodes and the second subset of impedance measurement electrodes.

In another form, the invention also relates to a tissue impedance measuring device for a biopsy system. The tissue impedance measuring device includes a tissue sample collection receptacle, a driver mechanism, a first subset of impedance measurement electrodes, a second subset of impedance measurement electrodes, and an impedance measurement circuit. The tissue sample collection receptacle is configured to receive a tissue sample. The tissue sample collection receptacle has an arrangement of compression plates. The arrangement of compression plates includes a first compression plate and a second compression plate. The arrangement of compression plates is configured to compress the tissue sample between the first compression plate and the second compression plate. The driver mechanism may be configured to move the first compression plate toward the second compression plate. The first subset of impedance measurement electrodes is on the first compression plate. The second subset of impedance measurement electrodes is on the second compression plate. The second subset of impedance measurement electrodes are opposed to and facing the first subset of impedance measurement electrodes. The impedance measurement circuit is connected to the first subset of impedance measurement electrodes of the first compression plate, and is connected to the second subset of impedance measurement electrodes of the second compression plate.

In some embodiments, as in the embodiment of the immediately preceding paragraph, for example, the first compression plate may be movable and the second compression plate is stationary. Optionally, the first and second compression plates can have the features of par. [0075] to [0078] above.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy system, comprising:
   a biopsy probe configured to sever tissue to acquire a tissue sample, the biopsy probe having a biopsy needle portion, the biopsy needle portion having a proximal end, a distal end, and a lumen;
   a vacuum source coupled to the lumen, the vacuum source configured to generate a vacuum to transport the tissue sample through the lumen and expel the tissue sample from the lumen at the proximal end of the biopsy needle portion;

an arrangement of compression plates configured to receive the tissue sample from the proximal end of the biopsy probe and operable to compress the tissue sample, the arrangement of compression plates having a plurality of impedance measurement electrodes, wherein the arrangement of compression plates receive the tissue sample between two opposing compression plates and at least one plate moves to compress the tissue sample between the two opposing compression plates; and an impedance measurement circuit connected to the plurality of impedance measurement electrodes.

2. The biopsy system according to claim 1, wherein the arrangement of compression plates is located in a tissue sample collection receptacle.

3. The biopsy system according to claim 1, wherein the arrangement of compression plates is located distal to the vacuum source.

4. The biopsy system according to claim 1, wherein the arrangement of compression plates comprises a driver mechanism, the driver mechanism configured to move the at least one plate to effect compression of the tissue sample.

5. The biopsy system according to claim 1, wherein the arrangement of compression plates comprises the at least one plate, a stationary plate, and a driver mechanism, the driver mechanism configured to move the movable plate toward the stationary plate.

6. The biopsy system according to claim 4, wherein the driver mechanism comprises a cylinder having a piston coupled to the at least one plate to move the at least one plate, and the piston being moved via one of a pneumatic force and a hydraulic force.

7. The biopsy system according to claim 4, wherein the driver mechanism comprises one of a mechanical device and an electromechanical device.

8. The biopsy system according to claim 1, wherein each compression plate of the arrangement of compression plates has at least one impedance measurement electrode.

9. The biopsy system according to claim 1, wherein one compression plate of the arrangement of compression plates has at least two impedance measurement electrodes.

10. The biopsy system according to claim 1, wherein the impedance measurement circuit is electrically coupled to each of the plurality of impedance measurement electrodes, the impedance measurement circuit configured to actuate at least one pair of impedance measurement electrodes of the plurality of impedance measurement electrodes.

11. The biopsy system according to claim 1, wherein the arrangement of compression plates includes a first compression plate and a second compression plate, the first compression plate having a first subset of impedance measurement electrodes of the plurality of impedance measurement electrodes, and the second compression plate having a second subset of impedance measurement electrodes of the plurality of impedance measurement electrodes.

12. The biopsy system according to claim 11, wherein the impedance measurement circuit is electrically coupled to each of the first subset of impedance measurement electrodes and the second subset of impedance measurement electrodes, the impedance measurement circuit having a processor circuit that executes program instructions to activate at least one impedance measurement electrode from the first subset of impedance measurement electrodes and to activate at least one impedance measurement electrode from the second subset of impedance measurement electrodes, to facilitate impedance measurement.

13. The biopsy system according to claim 11, wherein:

the first subset of impedance measurement electrodes is arranged in a first array pattern and the second subset of impedance measurement electrodes is arranged in a second array pattern;

the first subset of impedance measurement electrodes of the first array pattern is opposed to the second subset of impedance measurement electrodes of the second array pattern;

the processor circuit executes program instructions to sequentially activate opposed pairs of impedance measurement electrodes of the first subset of impedance measurement electrodes and the second subset of impedance measurement electrodes; and the processor circuit executes program instructions to simultaneously activate multiple opposed pairs of impedance measurement electrodes of the first subset of impedance measurement electrodes and the second subset of impedance measurement electrodes.

14. A biopsy system, comprising:

a biopsy probe configured to sever tissue to acquire a tissue sample, the biopsy probe having a biopsy needle portion, the biopsy needle portion having a proximal end, a distal end, and a lumen;

a vacuum source coupled to the lumen, the vacuum source configured to generate a vacuum to transport the tissue sample through the lumen and expel the tissue sample at the lumen at the proximal end of the biopsy needle portion;

a tissue sample collection receptacle configured to receive the tissue sample from the proximal end of the biopsy probe, the tissue sample collection receptacle having an arrangement of compression plates, the arrangement of compression plates including a movable compression plate and a stationary compression plate, the arrangement of compression plates operable to compress the tissue sample between the movable compression plate and the stationary compression plate;

a driver mechanism configured to move the movable compression plate toward the stationary compression plate;

a first subset of impedance measurement electrodes on the movable compression plate;

a second subset of impedance measurement electrodes on the stationary compression plate, the second subset of impedance measurement electrodes being opposed to and facing the first subset of impedance measurement electrodes; and an impedance measurement circuit connected to the first subset of impedance measurement electrodes of the movable compression plate, and connected to the second subset of impedance measurement electrodes of the stationary compression plate.

15. The biopsy system according to claim 14, wherein the impedance measurement circuit is electrically coupled to each of the first subset of impedance measurement electrodes and the second subset of impedance measurement electrodes, the impedance measurement circuit having a processor circuit that executes program instructions to activate at least one impedance measurement electrode from the first subset of impedance measurement electrodes and to activate at least one impedance measurement electrode from the second subset of impedance measurement electrodes, to facilitate impedance measurement.

16. The biopsy system according to claim 14, wherein the first subset of impedance measurement electrodes is arranged in a first array pattern and the second subset of impedance measurement electrodes is arranged in a second array pattern.

17. The biopsy system according to claim 14, wherein the first subset of impedance measurement electrodes is arranged in a first array pattern and the second subset of impedance measurement electrodes is arranged in a second array pattern, and wherein the first subset of impedance measurement electrodes of the first array pattern is opposed to the second subset of impedance measurement electrodes of the second array pattern, and wherein the processor circuit executes program instructions to sequentially activate opposed pairs of impedance measurement electrodes of the first subset of impedance measurement electrodes and the second subset of impedance measurement electrodes.

18. The biopsy system according to claim 15, wherein the processor circuit executes program instructions to simultaneously activate multiple opposed pairs of impedance measurement electrodes of the first subset of impedance measurement electrodes and the second subset of impedance measurement electrodes.

19. A tissue impedance measuring device for a biopsy system, comprising:

a tissue sample collection receptacle configured to receive a tissue sample, the tissue sample collection receptacle comprising:

a housing couplable to a biopsy device and having an opening sized to receive a cutting cannula of the biopsy device so as to receive the tissue sample through the opening; and an arrangement of compression plates positioned within the housing, the arrangement of compression plates including a first compression plate and a second compression plate, the arrangement of compression plates operable to compress the tissue sample between the first compression plate and the second compression plate;

a driver mechanism configured to move the first compression plate toward the second compression plate;

a first subset of impedance measurement electrodes on the first compression plate; and a second subset of impedance measurement electrodes on the second compression plate, the second subset of impedance measurement electrodes being opposed to and facing the first subset of impedance measurement electrodes; and an impedance measurement circuit connected to the first subset of impedance measurement electrodes of the first compression plate, and connected to the second subset of impedance measurement electrodes of the second compression plate.

20. The tissue impedance measuring device according to claim 19, wherein the first compression plate is movable and the second compression plate is stationary.

\* \* \* \* \*